Figure 1:
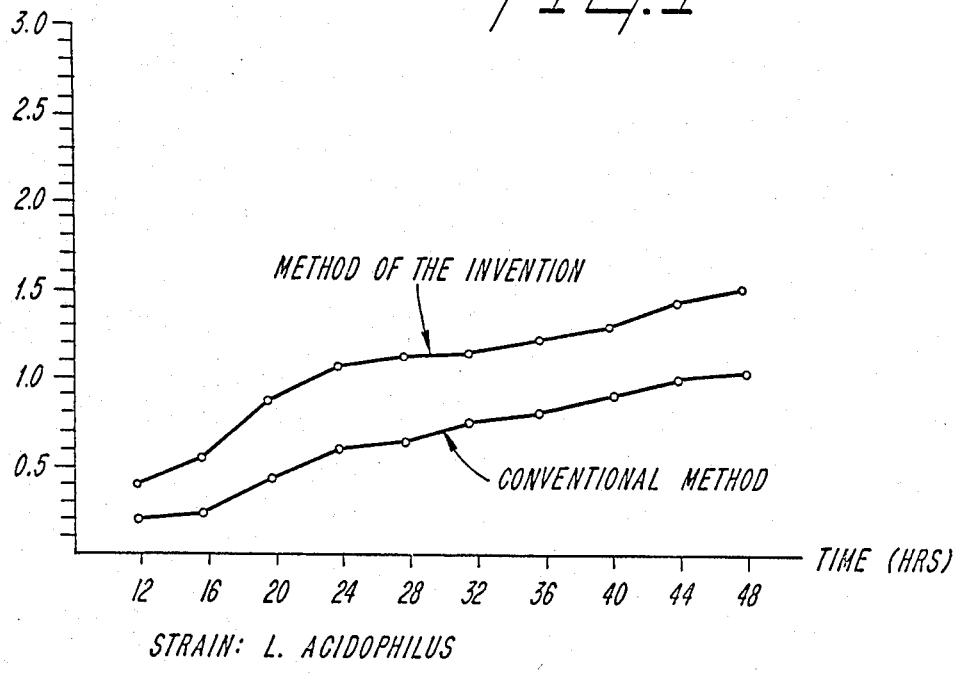

United States Patent [19]

Lee et al.

[11] Patent Number: 4,524,136
[45] Date of Patent: Jun. 18, 1985

[54] PROCESS FOR PREPARING A COSMETIC MATERIAL

[75] Inventors: Byung S. Lee; Chang K. Kim, both of Seoul, Rep. of Korea

[73] Assignee: Pacific Chemical Industrial Co., Ltd., Seoul, Rep. of Korea

[21] Appl. No.: 444,187

[22] Filed: Nov. 24, 1982

Related U.S. Application Data

[63] Continuation of Ser. No. 144,876, Apr. 29, 1980, abandoned.

[30] Foreign Application Priority Data

May 1, 1979 [KR] Rep. of Korea ............... 1979-1389

[51] Int. Cl.$^3$ .............................................. C12P 7/56
[52] U.S. Cl. .................................... 435/139; 435/272; 435/853
[58] Field of Search ............... 435/139, 272, 853–856, 435/885

[56] References Cited

FOREIGN PATENT DOCUMENTS 579591 7/1959 Canada ................................ 435/853

Primary Examiner—Hiram H. Bernstein
Attorney, Agent, or Firm—Finnegan, Henderson, Farabow, Garrett & Dunner

[57] ABSTRACT

A process for preparing a transparent cosmetic material having a moisturizing effect in which lactic acid and casein hydrolysate formation are carried out simultaneously in skim milk by lactic acid bacteria and proteases and, subsequently, sterilization of the lactic acid bacteria and inactivation of the proteolytic enzyme are carried out simultaneously.

7 Claims, 4 Drawing Figures

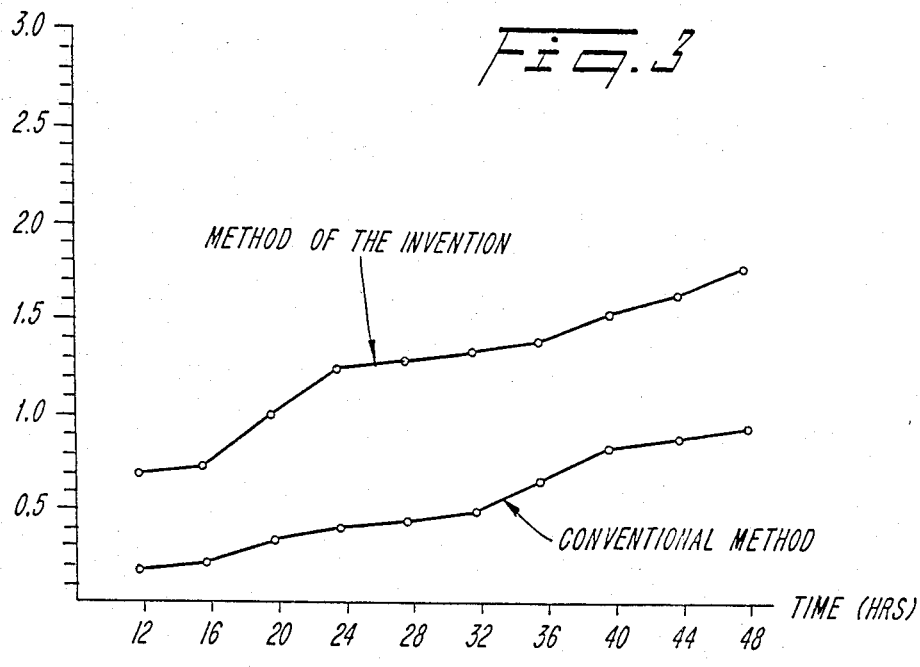
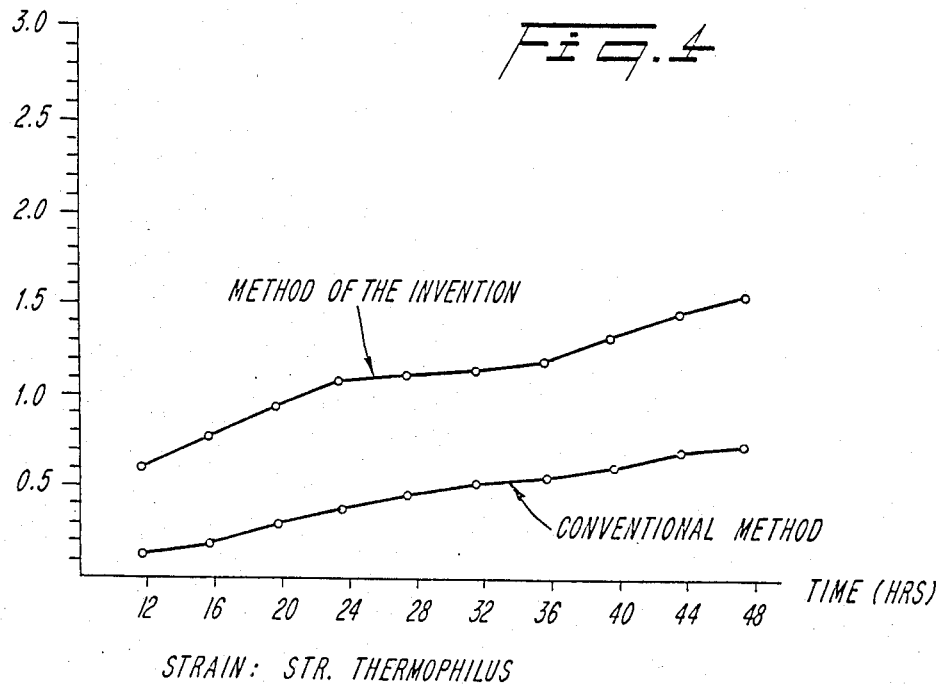

PROCESS FOR PREPARING A COSMETIC MATERIAL

This is a continuation of application Ser. No. 144,876, filed Apr. 29, 1980 and now abandoned.

The present invention relates to a novel, transparent cosmetic material having a moisturizing effect.

An object of the present invention is to provide a simpler process for preparing a cosmetic material.

Another object of the invention is to provide a cosmetic material which can be used for various commerical cosmetics.

A further object of the invention is to provide a cosmetic material useful as a high-moisturizing agent.

These and other objects and advantages of the present invention will be apparent to persons skilled in the art from the following description.

It is known that milk, skim milk and skim milk powder have been used in the past as a cosmetic material for the skin. All of these materials contain casein, a milk protein which belongs to the class of phosphoproteins and contains essential amino acids and sulfur-containing amino acids. Because of these ingredients, casein is useful as a moisturizing agent and a skin nutrient.

Moreover, it has been discovered recently that lactate is a natural moisturizing factor (N.M.F.). Thus, sterilized-fermented milk obtained by lactic fermentation with lactic acid bacteria has been used as a cosmetic material.

Because it contains water-insoluble casein, however, sterilized-fermented milk is not transparent. Further, because it is a polymeric material, casein is poor in absorption and adsorption to the skin.

To overcome these problems, the casein in sterilized-fermented milk has to be decomposed to a water-soluble casein-hydrolysate to obtain a transparent cosmetic material which also has a high moisturizing effect on skin.

Conventionally, therefore, the casein in sterilized-fermented milk is rendered water-soluble by four steps: (1) a lactic acid fermentation process; (2) a lactic acid bacteria sterilizing process; (3) a proteolytic enzyme reacting process; and (4) an enzyme inactivating process. Unfortunately, these four steps require long times, complicated processing and high production costs.

In the present invention, the inventors have developed a simpler, two-step process for preparing desired cosmetic materials.

In the first step, both lactic fermentation by lactic acid bacteria and decomposition of casein by proteolytic enzyme in skim milk or skim milk mixed with skim milk powder are carried out simultaneously.

In the second step, both sterilization of the lactic acid bacteria and inactivation of the proteolytic enzyme are carried out simultaneously.

In the first step, lactic acid and casein hydrolysate are formed by the potentiation of lactic acid bacteria and protease.

Lactic acid bacteria useful in the present invention include *L. acidophilus, L. burgaricus, L. casei* and *Str. thermophilus*. Both neutral and acid protease can be used.

The protease converts the casein from a water-insoluble substance into water-soluble casein hydrolysate and, as a result, a transparent solution can be obtained that is suitable to be used for skin-beauty cosmetics. As is well known, casein is a substance having a molecular weight of from 20000 to 30000.

Further, in the first step, because pH changes in the skim milk occur during fermentation by lactic acid bacteria, both neutral protease and acid protease are preferably used. As fermentation begins, the pH of the skim milk is 6.4±0.4 and the neutral protease reacts. As the fermentation process proceeds, lactic acid is produced and the pH of the skim milk is lowered to 3.0 to 4.5, in which pH range the acid protease reacts.

The simultaneous achievement of lactic acid fermentation and casein decomposition in skim milk, or in skim milk mixed with skim milk powder is possible because about 35°–40° C. is both the most preferred fermenting temperature range for lactic acid bacteria and also a suitable reaction temperature for protease.

The fermenting time of the process is shortened because decomposition of casein by protease accelerates the growth of lactic acid bacteria.

The acidity of lactic acid produced by the present invention and that of lactic acid produced by a conventional process are shown in Table 1.

Figure 2:
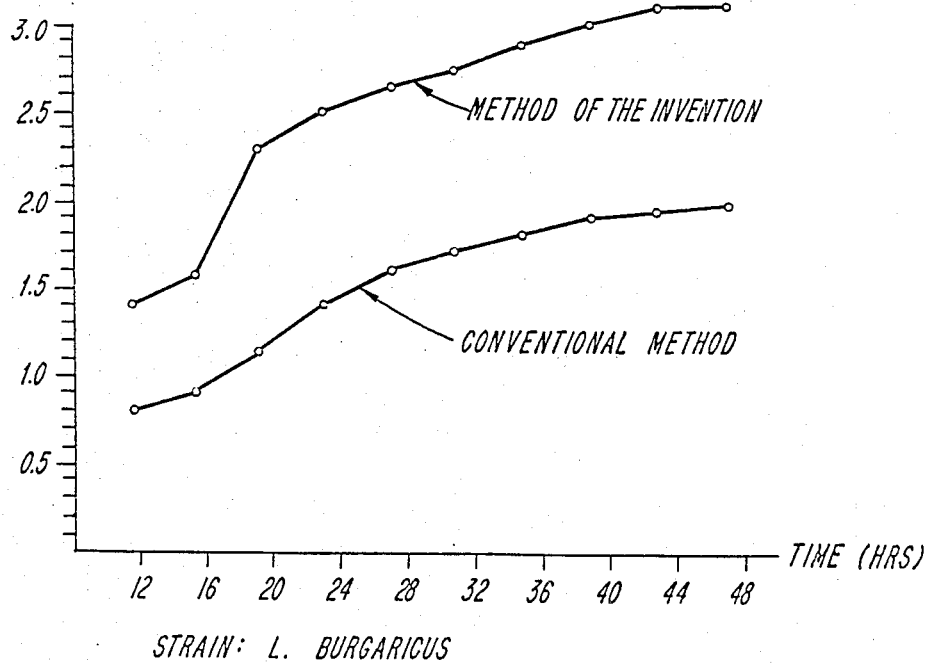

FIGS. 1, 2, 3 and 4 graphically represent the results in Table 1.

TABLE 1

| Lacticacid bacteria | process | Acidity of lactic acid produced by fermentation with various lactic acid bacteria (%) time (hrs) | | | | | | | | | |
|---|---|---|---|---|---|---|---|---|---|---|---|
| | | 12 | 16 | 20 | 24 | 28 | 32 | 36 | 40 | 44 | 48 |
| L. acidophilus | convention | 0.20 | 0.23 | 0.43 | 0.55 | 0.58 | 0.64 | 0.70 | 0.91 | 0.93 | 1.00 |
| | invention | 0.45 | 0.54 | 0.88 | 1.04 | 1.08 | 1.10 | 1.22 | 1.23 | 1.41 | 1.50 |
| L. burgaricus | convention | 0.80 | 0.90 | 1.28 | 1.38 | 1.66 | 1.70 | 1.78 | 1.87 | 1.90 | 1.95 |
| | invention | 1.37 | 1.58 | 2.32 | 2.51 | 2.61 | 2.69 | 2.87 | 2.95 | 3.03 | 3.03 |
| L. casei | convention | 0.14 | 0.18 | 0.32 | 0.41 | 0.43 | 0.48 | 0.68 | 0.76 | 0.82 | 0.92 |
| | invention | 0.71 | 0.76 | 1.03 | 1.23 | 1.25 | 1.24 | 1.36 | 1.56 | 1.60 | 1.74 |
| Str. thermophilus | convention | 0.14 | 0.16 | 0.28 | 0.35 | 0.41 | 0.45 | 0.50 | 0.56 | 0.63 | 0.62 |
| | invention | 0.60 | 0.76 | 0.87 | 1.03 | 1.04 | 1.08 | 1.14 | 1.25 | 1.35 | 1.41 |

With reference to the results in Table 1 corresponding to the present invention, skim milk (8.5% as solids-non-fat content); a neutral protease (activity: 70000–80000(PU)$_{Tyr.}$$^{Cas.\ F.\ R./g}$); and an acid protease (activity: 4000–50000(PU)$_{Tyr.}$$^{Cas.\ F.\ R./g}$) were used. The acidity of lactic acid was titrated by 0.1N-NaOH, and the blank volume of titration was deducted from the consumed volume of titration and converted by the following expression:

$$\text{Acidity of lactic acid (\%)} = \frac{0.1N - \text{NaOH net volume of titration (ml)} \times f(\text{NaOH}) \times 0.009 \times 100}{\text{weight of test material (g)}}$$

Skim milk (8.5% as solids-non-fat content) or skim milk mixed with skim milk powder (9–25% as solids-non-fat content) is sterilized and cooled in a conventional manner, and then 2 to 3% of starter of L. burgaricus and, as the neutral protease, 0.1 to 5.0%, by weight, of one of the neutral proteases (activity: 70000–80000(PU)$_{Tyr.}$$^{Cas.\ F.\ R./g}$) and, as the acid protease, 0.1 to 3.0 by weight, of one of acid proteases (activity: 40000–50000(PU)$_{Tyr.}$$^{Cas.\ F.\ R./g}$) are inoculated, and then maintained at 35° to 40° C. for about 12 to 48 hours for fermentation and reaction with lactic bacteria and protease.

In the process, the neutral and acid proteases react corresponding to the pH change of said skim milk as hereinbefore described.

After completion of the first step, fermentation by lactic acid bacteria and decomposition of casein by proteases, the second step is performed. The mixture obtained from the first step is sterilized and inactivated by heating at about 75° C. for 30 minutes.

The dead bacteria and inactivated enzyme and other insoluble inorganic substances are removed by a filter press or by a continuous centrifugal separator after cooling.

50% NaOH and KOH solution is then added to the transparent filtrate obtained to adjust the pH to 6.1±0.1 with stirring.

The composition of the material obtained by the present invention is compared with that of a natural moisturizing factor in Table 2:

TABLE 2

| Components | material of the invention | Natural Moisture factor (N.M.F.) |
|---|---|---|
| Amino acid | 32.78 | 40.0 |
| Lactic acid | 29.27 | 12.0 |
| Sugars | 22.95 | 8.5 |
| Na | 5.14 | 5.0 |
| Ca | 0.70 | 1.5 |
| K | 4.29 | 4.0 |
| Mg | 0.12 | 1.5 |
| Phosphates | 0.45 | 0.5 |
| Urea, Uric acid | 0.08 | 1.5 |
| P.C.A. | | 12.0 |

As shown in Table 2, the composition of the material obtained by the present invention is extremely similar to that of a natural skin moisturizing factor. Accordingly, the material obtained by the process of the present invention is valuable as a cosmetic material.

The material obtained by the process of the present invention was subjected to the animal test and patch test of the human body to determine its safety.

In the animal test, the Acute Oral Toxicity was tested on eight Albino rats by administering 0.5 ml of the inventive material per 10 grams, by body weight, of Albino rat every day for 30 days. The rats showed almost no change of body weight and no other changes.

The first stimulatative test of the eye mucous membrane of rabbits was done in the manner of Draize.

The results of this test are shown in Table 3:

TABLE 3

| | Rabbit No. | | | | | | | | | | | | | | | | | | | | | | | |
|---|---|---|---|---|---|---|---|---|---|---|---|---|---|---|---|---|---|---|---|---|---|---|---|---|
| | 1 | | | | | | 2 | | | | | | 3 | | | | | | 4 | | | | | |
| | after hrs | | | | | | | | | | | | | | | | | | | | | | | |
| | 1 | 24 | 48 | 72 | 96 | 168 | 1 | 24 | 48 | 72 | 96 | 168 | 1 | 24 | 48 | 72 | 96 | 168 | 1 | 24 | 48 | 72 | 96 | 168 |
| Cornea | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Iris | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Conjunctiva | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Average | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | Rabbit No. | | | | | | | | | | | | | | | | | | | | | | | |
| | 5 | | | | | | 6 | | | | | | 7 | | | | | | 8 | | | | | |
| | after hrs | | | | | | | | | | | | | | | | | | | | | | | |
| | 1 | 24 | 48 | 72 | 96 | 168 | 1 | 24 | 48 | 72 | 96 | 168 | 0 | 0 | 0 | 0 | 0 | 0 | 0 | 0 | 0 | 0 | 0 | 0 |
| Cornea | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Iris | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Conjunctiva | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Average | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

The test solution was prescribed by using 50% of the inventive material by volume. 0.1 ml of the prescribed solution were tested with the right eye in contrast to the left eye to determine the stimulativity.

The results of the Patch Test with the skin of a human body using the material produced by the process of the present invention are shown in Table 4:

TABLE 4

| Sex | Age | Number of persons tested | After 30 minutes ± + ++ +++ | after 48 hrs ± + ++ +++ |
|---|---|---|---|---|
| Male | 15–20 | 17 | . . . . | . . . . |
| | 20–29 | 36 | . . . . | . . . . |
| | 30–39 | 21 | 1 . . . | . . . . |
| | 40–49 | 13 | . . . . | . . . . |
| Female | 15–20 | 32 | . . . . | . . . . |
| | 20–29 | 74 | . . . . | . . . . |
| | 30–39 | 27 | . . . . | . . . . |
| | 40–49 | 18 | . . . . | . . . . |
| Total | | 238 | 1 | |

(Note)
±: light red spots,
+: red spots,
++: dropsy,
+++: small bister

Table 4 shows that the results of the Patch Test on 238 persons are overwhelmingly negative.

EXAMPLE 1

After sterilizing and cooling 1 ltr. of skim milk (8.5% as solids-non-fat content) in a conventional manner, 2–3% of starter of L. burgaricus, 0.8% of bacterial neutral protease (activity: 78,000(PU)$_{Tyr.}$$^{Cas.\ F.\ R./g}$) of source of Bacillus subtilis and 0.6% of acid protease (activity: 46,000(PU)$_{Tyr.}$$^{Cas.\ F.\ R./g}$) of source of Aspergillus are added to the solution. After maintaining the resultant mixture at 37° C. for 24 hrs., the mixture is heated at about 75° C. for 30 minutes and, after cooling, a filtrate is obtained by using a filter press and a continuous centrifugal separator. Then 50% NaOH and KOH solution is added to the transparent filtrate obtained to adjust its pH to 6.1±0.1 with stirring.

EXAMPLE 2

1. lt. of skim milk mixed with skim milk powder (15% as solids-non-fat content) is sterilized and cooled and, to this solution are added 2-3% of the starter of *L. burgaricus*, 1.8% of neutral protease (activity: 70,000(PU)$_{Tyr.}$$^{Cas. F. R./g}$) of the source of Aspergillus and 1.0% of acid protease (activity: 46,000(PU)$_{Tyr.}$$^{Cas. F. R./g}$) of the source of Aspergillus. After maintaining the resultant mixture at 37° C. for 18 hrs., the mixture is heated at about 75° C. for 30 minutes and, after cooling, a filtrate is obtained by using a filter press and a continuous centrifugal separator. 50% NaOH and KOH solution is added to the transparent filtrate obtained to adjust its pH to 6.1±0.1 with stirring.

EXAMPLE 3

1 lt. of the mixture of skim milk mixed with skim milk powder (17% as solids-non-fat content) is sterilized and cooled in a conventional manner and then 2-3% of the starter of *L. burgaricus* and 2.8% of neutral protease (activity: 45,000(PU)$_{Tyr.}$$^{Cas. F. R./g}$) of Streptomycetes, and 1.2% of acid protease (activity: 46,000(PU)$_{Tyr.}$$^{Cas. F. R./g}$) and, after maintaining the resultant mixture at 37° C. for 30 hours, the mixture is heated at about 75° C. for 30 minutes and, after cooling said mixture, a filtrate is obtained by using a filter press and a continuous centrifugal separator. 50% NaOH and KOH is then added to the transparent filtrate obtained to adjust its pH to 6.0±0.1 with stirring.

EXAMPLE 4

1. lt. of skim milk mixed with skim milk powder (20% as solids-non-fat content) is sterilized and cooled in a conventional manner and to this solution, 2-3% of the starter of *L. burgaricus*, 19.0% of crude papain (activity: 7,000(PU)$_{Tyr.}$$^{Cas. F. R./g}$), and 1.4% of acid protease (activity: 46,000(PU)$_{Tyr.}$$^{Cas. F. R./g}$) of Aspergillus are added. After maintaining the resultant mixture at 37° C. for 36 hours, the mixture is heated at about 75° C. for 30 minutes and, after cooling, a filtrate is obtained by using a filter press and a continuous centrifugal separator. 50% NaOH and KOH solution is then added to the transparent filtrate obtained to adjust its pH to 6.0±0.1 with stirring.

EXAMPLE 5

1 lt. of skim milk mixed with skim milk powder (25% as solids-non-fat content) is sterilized and cooled and, to this solution, 2-3% of the starter of *L. burgaricus* and 2.8% of Trypsin (activity: 65,000(PU)$_{Tyr.}$$^{Cas. F. R./g}$), 1.7% of acid protease (activity: 46,000(PU)$_{Tyr.}$$^{Cas. F. R./g}$) of Aspergillus are are added and, after maintaining the resultant mixture at 37° C. for 48 hours, the mixture is heated at about 75° C. for 30 mintues and, after cooling, a filtrate is obtained by using a filter press and a continuous centrifugal separator. 50% NaOH and KOH solution is then added to the transparent filtrate obtained to adjust the pH to 6.1±0.1 with stirring.

Prescription examples for using the material of the present invention in cosmetics are:

| Prescription example A: Skin Lotion | | |
|---|---|---|
| | A$_1$ | A$_2$ |
| Ethyl alcohol | 10 | 10 |
| Tween 80 | 1.0 | 1.0 |
| P.G. | 3.0 | 3.0 |
| Citric acid | 0.05 | 0.05 |
| Perfume | proper amount | proper amount |
| Dye | proper amount | proper amount |
| material of the invention | 3.0 | — |
| Methyl paraben | 0.05 | 0.05 |
| Purified water | To 100 | To 100 |

| Prescription example B: Lotion | | |
|---|---|---|
| | B$_1$ | B$_2$ |
| Cetyl alcohol | 1.5 | 1.5 |
| Stearic acid | 2.0 | 2.0 |
| Synthetic gas oil | 0.5 | 0.5 |
| Lanolin oil | 1.0 | 1.0 |
| Mineral oil | 8.0 | 8.0 |
| 2-octyl dodecanol | 2.0 | 2.0 |
| Tween 60 | 2.0 | 2.0 |
| Arlacel 60 | 1.0 | 1.0 |
| Proylene glycol | 5.0 | 5.0 |
| Sorbitol | 3.0 | 3.0 |
| Perfume | 0.2 | 0.2 |
| Methyl paraben | 0.15 | 0.15 |
| Propyl paraben | 0.05 | 0.05 |
| Hydroxy propylmethyl cellulose | 0.2 | 0.2 |
| Triethanolamine | 0.5 | 0.5 |
| material of the invention | 3.0 | — |
| Purified water | To 100 | To 100 |

| Perscription example C: Cream | | |
|---|---|---|
| | C$_1$ | C$_2$ |
| Cetyl alcohol | 3.0 | 3.0 |
| Stealic acid | 4.0 | 4.0 |
| Beeswax | 1.5 | 1.5 |
| Lanolin oil | 1.0 | 1.0 |
| 2-octyl dodecanol | 8.0 | 8.0 |
| isopropyl myristate | 10.0 | 10.0 |
| Olive oil | 3.0 | 3.0 |
| Tween 100 | 2.0 | 2.0 |
| Arlacel 60 | 1.0 | 1.0 |
| Propylene glycol | 5.0 | 5.0 |
| Sorbitol | 3.0 | 3.0 |
| Perfume | 0.2 | 0.2 |
| Methylparaben | 0.15 | 0.15 |
| Propylparaben | 0.05 | 0.05 |
| Triethanolamine | 0.7 | 0.7 |
| material of the invention | 5.0 | — |
| Purified water | to 100 | to 100 |

In these prescription examples, items A1, B1, and C1 which used the material of the invention were compared with items A2, B2, and C2 which did not use this material with respect to usability, moisturizing effect, skin resilience and skin cornification. To make the comparisons, 50 females, 18 to 45 years old, applied the prescribed items to their faces and hands after washing in the morning and evening for one month. The results are reported in Table 5.

TABLE 5

| Products | Usability | | | Moisturizing effect | | | SKIN RESILIENCE | | | SKIN CORNIFICATION | | |
|---|---|---|---|---|---|---|---|---|---|---|---|---|
| | better | same | inferior | better | same | inferior | better | same | inferior | better | same | inferior |
| $A_1$ (in comparison with $A_2$) | 4 | 44 | 2 | 43 | 7 | — | 42 | 8 | — | 35 | 15 | — |
| $B_1$ (in comparison with $B_2$) | 3 | 46 | 1 | 41 | 9 | — | 37 | 9 | 4 | 34 | 15 | 1 |
| $C_1$ (in comparison with $C_2$) | 3 | 46 | 1 | 42 | 8 | — | 41 | 7 | 2 | 37 | 13 | — |

What is claimed is:

1. A process for preparing a cosmetic material comprising the steps of:
   (a) simultaneously and coextensively carrying out in skim milk the processes of lactic acid formulation by lactic acid bacteria and decomposition of casein by proteases in a temperature range of about 35° to 40° C. for 12 to 48 hours; and
   (b) simultaneously carrying out the processes of sterilization of said lactic acid bacteria and inactivation of said proteases at about 75° C. for 30 minutes to produce a cosmetic material.

2. The process of claim 1 in which the solids-non-fat content of said skim milk is 8.5 to 25% by weight.

3. The process of claim 1 wherein said lactic acid bacteria is selected from the group consisting of *Lactobacillus burgaricus, Lactobacillus acidophilus, Lactobacillus casein* and *Streptococcus thermophilus.*

4. The process of claim 1 wherein both neutral and acid proteases are used in the decomposition of said casein.

5. The process of claim 4 wherein said neutral protease is selected from the group consisting of bacterial neutral protease, fungus neutral protease, streptomyces protease, papain and tyrpsin.

6. The process of claim 4 wherein said acid protease is fungus acid protease.

7. A process for preparing a cosmetic material consisting of the steps of:
   (a) simultaneously carrying out in skim milk the processes of lactic acid fermentation by lactic acid bacteria and decomposition of casein by proteases in a temperature range of about 35° to 40° C. for 12 to 48 hours; and
   (b) simultaneously carrying out the processes of sterilization of said lactic acid bacteria and inactivation of said proteases at about 75° C. for 30 minutes to produce a cosmetic material.

* * * * *